(12) United States Patent
Aichinger et al.

(10) Patent No.: US 6,617,470 B1
(45) Date of Patent: Sep. 9, 2003

(54) METHOD FOR ESTERIFYING (METH) ACRYLIC ACID WITH AN ALKANOL

(75) Inventors: Heinrich Aichinger, Mannheim (DE); Holger Herbst, Frankenthal (DE); Gerhard Nestler, Ludwigshafen (DE); Jürgen Schröder, Ludwigshafen (DE); Stefan Beckmann, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/831,349

(22) PCT Filed: Nov. 5, 1999

(86) PCT No.: PCT/EP99/08503

§ 371 (c)(1),
(2), (4) Date: May 11, 2001

(87) PCT Pub. No.: WO00/27789

PCT Pub. Date: May 18, 2000

(30) Foreign Application Priority Data

Nov. 11, 1998 (DE) .......................... 198 51 984

(51) Int. Cl.⁷ .................. C07C 69/54; C07C 67/00; C07C 57/18; C07C 33/34; C07C 29/20
(52) U.S. Cl. .............. 560/205; 560/216; 562/598; 562/599; 568/715; 568/835; 568/876
(58) Field of Search .................. 560/205, 212; 562/598, 599; 568/835, 876

(56) References Cited

U.S. PATENT DOCUMENTS

| | | | | | |
|---|---|---|---|---|---|
| 3,882,167 A | * | 5/1975 | Lohmar et al. | ............ | 560/205 |
| 4,250,328 A | * | 2/1981 | Fujita et al. | ............... | 560/205 |
| 4,329,492 A | * | 5/1982 | Andoh et al. | ............... | 560/205 |
| 4,435,594 A | * | 3/1984 | Matsumura et al. | ........ | 560/205 |
| 4,733,004 A | * | 3/1988 | Pascoe | ........................ | 560/205 |
| 5,910,603 A | * | 6/1999 | Aichinger et al. | .......... | 560/205 |

FOREIGN PATENT DOCUMENTS

EP 0779268 A1 * 6/1997

* cited by examiner

Primary Examiner—Alan L. Rotman
Assistant Examiner—Taylor V. Oh
(74) Attorney, Agent, or Firm—Oblon, Spivak, McClelland, Maier & Neustadt, P.C.

(57) ABSTRACT

In a process for esterifying (meth)acrylic acid with an alkanol in the presence of an esterification catalyst, in which unconverted starting compounds and (meth)acrylic ester to be formed are separated off by distillation and an oxyester-containing bottom product is formed, the bottom product is first separated off and then the oxyesters contained in it are cleaved in the presence of a relatively long-chain alkylbenzenesulfonic acid at elevated temperatures.

24 Claims, No Drawings

METHOD FOR ESTERIFYING (METH)ACRYLIC ACID WITH AN ALKANOL

The present invention relates to a process for esterifying (meth)acrylic acid with an alkanol in the presence of an esterification catalyst, in which unconverted starting compounds and (meth)acrylic ester formed are removed from the reaction mixture by distillation, leaving behind an oxyester-containing bottom product, the bottom product is separated off and the oxyesters contained therein are thereafter cleaved in the presence of at least one acid catalyst by the action of elevated temperatures.

In this application, the term "(meth)acrylic acid" is an abbreviation for acrylic or methacrylic acid.

Furthermore, the term "oligomeric (meth)acrylic acid" used in the further course of this application means the Michael adducts of (meth)acrylic acid with itself and with the resulting secondary products. Such Michael adducts may be characterized by the formula (III),

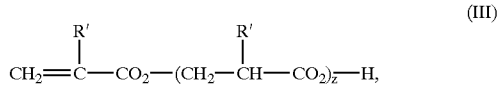

where z is an integer from 1 to 5 and R' is H or $CH_3$,
and are to be distinguished here from (monomeric) (meth)acrylic acid and from (meth)acrylic acid polymers (which are obtainable by free radical polymerization of (meth)acrylic acid). The essential feature is that the Michael addition reaction of (meth)acrylic acid with itself and its resulting secondary products is reversible. Oligomeric (meth)acrylic acid is obtained, for example, in the distillative treatment of (for example crude) (meth)acrylic acid (the term "crude" indicates a small amount of, in particular, aldehydic impurities still present) in the bottom product (cf. for example DE-A 22 35 326).

Usually, the preparation of alkyl esters of (meth)acrylic acid by esterifying (meth)acrylic acid with alkanols at elevated temperature is carried out in the liquid phase with or without solvents and in the presence of, as a catalyst, acids other than (meth)acrylic acid (cf. for example DE-A 23 39 519). The disadvantage of this method of preparation is that, as secondary reactions under the abovementioned esterification conditions, still unconverted starting alcohol undergoes addition at the ethylenically unsaturated double bond of already formed alkyl (meth)acrylate (Michael addition reaction) with formation of a compound of the formula I below and still unconverted (meth)acrylic acid undergoes addition at said double bond with formation of a compound of the formula II.

Successive multiple addition is also possible. Furthermore, mixed types can occur. These adducts (alkoxyesters and acyloxyesters) are referred to as oxyesters for short:

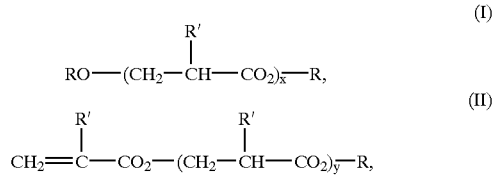

where x and y are integers from 1 to 5,
R is alkyl and
R' is R or $CH_3$.

The problem of oxyester formation is particularly pronounced in the preparation of esters of acrylic acid, the oxyesters mainly formed being the alkoxypropionic esters and the acyloxypropionic esters where x and y are 1. In the preparation of esters of methacrylic acid, the oxyester formation takes place to a lesser extent. The formation of oxyesters is described, inter alia, in DE-A 23 39 529 and in U.S. Pat. No. 5,734,075. The above publications confirm that the formation of oxyesters takes place essentially independently of the special esterification conditions. Of very particular importance is the oxyester formation in the preparation of acrylic esters of $C_1$- to $C_8$-alkanols, in particular of $C_4$- to $C_8$-alkanols, very particularly in the preparation of n-butyl acrylate and 2-ethylhexyl acrylate (for which reason the present invention is used in particular in connection with these esterifications).

Typical of the oxyesters is that their boiling point is above the boiling points of starting acid, starting alcohol, desired esters formed and any organic solvent present.

The working up of any desired esterification reaction mixture is usually carried out by separating unconverted starting compounds and resulting desired esters from the reaction mixture by distillation, the acid catalyst used for the esterification being separated off beforehand, if required, by extraction by means of water and/or aqueous alkali (cf. for example Ullmann's Encyclopedia of Industrial Chemistry, Vol. A1, 5th Ed., VCH, page 167 et seq.). The bottom product remaining in such working up by distillation contains the oxyesters, which result in considerably lower yields.

The prior art (e.g. DE-A 19 701 737, DE-A 19 536 191, DE-A 19 536 184, DE-A 19 547 485, DE-A 19 547 459 and CN-A 1063678) therefore contains various processes which cleave the oxyesters contained in the bottom product separated off, in the presence of at least one acid catalyst by the action of elevated temperatures, and separate off the resulting cleavage products, preferably by evaporation. Recommended suitable acidic cleavage catalysts are protic acids other than monomeric and oligomeric (meth)acrylic acid (acid strength>that of (meth)acrylic acid), for example mineral acids, such as sulfuric acid or phosphoric acid, and organic acids, such as methanesulfonic acid or p-toluenesulfonic acid. These definitions also apply to this application.

The disadvantage of the cleavage processes of the prior art is however that the resulting cleavage residue is generally highly viscous and as a rule contains solids.

Consequently, the cleavage residue is scarcely pumpable and can therefore be disposed of only with difficulty. Moreover, the generally tar-like solid is deposited on the wall surfaces in the course of time (fouling), which, for example, reduces the passage of heat or can lead to blockages, making it necessary to clean the wall surfaces from time to time.

U.S. Pat. No. 5,734,075 recommends carrying out the cleavage process in the absence of acidic cleavage catalysts and instead in the presence of oligomeric (meth)acrylic acid to reduce the abovementioned problems. However, the disadvantage of this procedure is that the cleavage, in particular in the case of bottom products which originate from esterifications with relatively long-chain alkanols, takes place comparatively slowly and gives only comparatively low conversions.

DE-A 19 536 184 recommends separating the oxyesters from the bottom product by distillation before cleaving in order to reduce said problems. The disadvantage of this procedure is the necessity of an additional distillation step.

The addition of a solvent as a diluent for reducing the viscosity problems has also been proposed. However, the requirement of an additional component is likewise disadvantageous.

It is an object of the present invention to provide a process for esterifying (meth)acrylic acid with an alkanol in the presence of an esterification catalyst, in which unconverted starting compounds and (meth)acrylic ester formed are removed from the reaction mixture by distillation, leaving behind an oxyester-containing bottom product, the bottom product is separated off and the oxyesters contained therein are thereafter cleaved in the presence of at least one acid catalyst by the action of elevated temperature, which process does not have the stated disadvantages of the processes of the prior art.

We have found that this object is achieved by a process for esterifying (meth)acrylic acid with an alkanol in the presence of an esterification catalyst, in which unconverted starting compounds and (meth)acrylic ester formed are removed from the reaction mixture by distillation, leaving behind an oxyester-containing bottom product, the bottom product is separated off and the oxyesters contained therein are thereafter cleaved in the presence of at least one acid catalyst by the action of elevated temperatures, wherein at least one aromatic sulfonic acid of the formula IV,

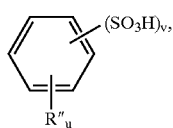

(IV)

where
R" independently of one another are each alkyl of six to twenty carbon atoms,
u is an integer from 1 to 3, and
v is 1 or 2,
is present as the at least one acid catalyst for cleaving the oxyesters.

The abovementioned sulfonic acids of the formula (IV) are disclosed, for example, in EP-A 521 488. u may be 1 or 2 or 3 and v may be 1 or 2. Frequently, the radicals R" are alkyl radicals of 8 to 16 or 10 to 14 carbon atoms. Suitable typical compounds (IV) are accordingly, for example, octylbenzenesulfonic acids, such as n-octylbenzenesulfonic acid, nonylbenzenesulfonic acids, such as n-nonylbenzenesulfonic acid, decylbenzenesulfonic acids, such as n-decylbenzenesulfonic acid, undecylbenzenesulfonic acids, such as n-undecylbenzenesulfonic acid, dodecylbenzenesulfonic acids, such as n-dodecylbenzenesulfonic acid, tridecylbenzenesulfonic acids, such as n-tridecylbenzenesulfonic acid, tetradecylbenzenesulfonic acids, such as n-tetradecylbenzenesulfonic acid, pentadecylbenzenesulfonic acids, such as n-pentadecylbenzenesulfonic acid, hexadecylbenzenesulfonic acids, such as n-hexadecylbenzenesulfonic acid, heptadecylbenzenesulfonic acids, such as n-heptadecylbenzenesulfonic acid, octadecylbenzenesulfonic acids, such as n-octadecylbenzenesulfonic acid, nonyldecylbenzenesulfonic acids, such as n-nonyldecylbenzenesulfonic acid, heptadecylbenzenesulfonic acids, such as n-heptadecylbenzenesulfonic acid, octadecylbenzenesulfonic acids, such as n-octadecylbenzenesulfonic acid, nonyldecylbenzenesulfonic acids, such as n-nonyldecylbenzenesulfonic acid, and eicosylbenzenesulfonic acids, such as n-eicosylbenzenesulfonic acid. According to the invention, it is of course also possible to use mixtures of compounds (IV). Such mixtures are used as a rule when compounds (IV) which are only of technical-grade purity are used. Examples of such technical-grade, commercially available compounds (IV) are the alkylbenzenesulfonic acids Bio-Soft® S-100 (average molecular weight about 318, average R" chain length=11.5 carbon atoms; manufacturer=Stepan Co.), AAS-985 (linear alkylbenzenesulfonic acid having an average alkyl chain length of $C_{11}$–$C_{12}$, manufacturer= Continental Chemical Co.), Vista SA 697 and Vista SA 597 (linear alkylbenzenesulfonic acids having an average molecular weight of 342 and 318, respectively, manufacturer=Vista Chemical Co.), Stepantan® H-100 (a branched dodecylbenzenesulfonic acid, manufacturer= Stepan Co.) and a technical-grade alkylbenzenesulfonic acid from Alfa Products Co., in which 1% by weight of R" comprises $C_{10}$, 40% by weight comprises $C_{11}$, 28% by weight comprises $C_{12}$ and 31% by weight comprises $C_{13}$.

In the novel process, the sulfonic acids (IV) to be used according to the invention can be employed both as sole acidic cleavage catalysts and as a mixture with the acidic cleavage catalysts recommended in the prior art cited (e.g. sulfuric acid, phosphoric acid, methanesulfonic acid and/or p-toluenesulfonic acid), i.e. the molar amount of the novel compounds (IV) may be, for example, $\geq 1$ mol %, $\geq 5$ mol %, 10 mol %, $\geq 15$ mol %, $\geq 25$ mol %, $\geq 50$ mol %, $\geq 75$ mol %, $\geq 90$ mol %, $\geq 95$ mol % or 100 mol %, based on the total amount of acidic cleavage catalysts used in the novel process. Preferably, the abovementioned amount of the novel compounds (IV) is at least 25 mol %, particularly preferably at least 50 mol %, very particularly preferably at least 75 mol % and particularly advantageously 100 mol %.

As a rule, the novel cleavage is carried out in the presence of a total amount of from 1 to 50, frequently from 1 to 40 or from 5 to 20, % by weight, based on the amount of the oxyesters to be cleaved, of acidic cleavage catalysts.

Furthermore, the novel cleavage can be carried out according to DE-A 19 547 459 or DE-A 19 547 485 in the additional presence of monomeric and/or oligomeric (meth) acrylic acid. The amount of such monomeric and/or oligomeric (meth)acrylic acid may be up to 50% by weight or more, based on the amount of oxyesters to be cleaved. Frequently, the abovementioned amount of monomeric and/ or oligomeric (meth)acrylic acid will be from 5 to 50 or from 10 to 40 or from 20 to 35% by weight.

Usually, the monomeric and/or oligomeric (meth)acrylic acid are added to the bottom product to be subjected to the cleavage in a conventional form stabilized by means of polymerization inhibitors. In a particularly simple manner, the oligomeric (meth)acrylic acid used may be the bottom product which is obtained in the distillative purification of crude (meth)acrylic acid and contains mainly compounds of the formula (III) (cf. for example DE-A 22 35 326). The presence of monomeric and/or oligomeric (meth)acrylic acid in the novel cleavage results in particular in reduced formation of ether and olefin byproducts.

In addition, according to DE-A 19 701 737, the novel cleavage of the bottom product can be carried out in the presence of water. The abovementioned amount of water is as a rule from 0.1 to 20, frequently from 1 to 10, % by weight, based on the amount of the oxyesters to be cleaved.

The bottom product to be cleaved and the compounds (IV) to be used according to the invention and any other acidic cleavage catalysts likewise to be added and monomeric and/or oligomeric (meth)acrylic acid and any water can be added to the bottom product to be cleaved before the latter is transferred to the cleavage reactor. However, they can also be fed separately to the cleavage reactor. A part or all of the acidic cleavage catalysts required according to the invention may also be the acidic esterification catalysts. According to an advantageous embodiment of the invention, the novel cleavage is carried out in the presence of molecular oxygen.

It is particularly advantageous if a stripping gas, which preferably contains molecular oxygen, is passed as an entraining agent for the cleavage products through the mixture to be cleaved in the novel process. The stripping gas used is advantageously air or a mixture of air with inert gas (e.g. nitrogen).

The cleavage temperature to be used according to the invention is as a rule from 140 to 260° C., frequently from 180 to 230° C. The novel cleavage is preferably carried out at atmospheric or reduced pressure (<1 bar), typically at from 500 to 700, frequently from 40 to 300, mbar (so that the cleavage products evaporate immediately).

If a stripping gas is passed through the cleavage mixture during the cleavage, its amount is usually 1–100 l per h per l. As a rule, the cleavage requires reaction times of from 1 to 15 hours. The conversion of the cleavage is usually ≧90% by weight.

For example, a simple heatable stirred reactor having double-jacket heating or heating coil or a forced-circulation evaporator, for example a falling film evaporator or flash evaporator, coupled with a dwell tank, can be used for carrying out the novel cleavage. For better separation of the cleavage products from the bottom product, a rectification apparatus mounted on the cleavage apparatus, for example a packed or tray column, may be expedient. This rectification apparatus is as a rule operated with stabilization with polymerization inhibitors (e.g. phenothiazine, hydroquinone monomethyl ether, hydroquinone, etc.). Of course, the bottom product to be cleaved and originating from the esterification is also stabilized against polymerization by means of polymerization inhibitors.

The reaction in the novel cleavage takes place, for example, by a procedure in which the bottom product to be cleaved is removed continuously from the distillative working-up of the esterification mixture and is fed, with the cleavage catalyst to be used according to the invention, any monomeric and/or oligomeric (meth)acrylic acid and any water, to the cleavage reactor. However, the reaction can also be carried out batchwise. Also possible is a semicontinuous reaction in which the bottom product to be cleaved and any additives to be added to said bottom product are added continuously to the cleavage reactor which contains the acidic cleavage catalyst, and the bottom product obtained in the cleavage is removed batchwise from the cleavage reactor only after the end of the cleavage.

The cleavage products formed in the novel cleavage (alkanol, alkyl (meth)acrylate and (meth)acrylic acid) are usually separated off continuously in vapor form and, in contrast to the process of U.S. Pat. No. 5,734,075, can be recycled directly to the esterification without intermediate purification. Of course, the recycling could however also be carried out according to U.S. Pat. No. 5,734,075.

If the esterification is carried out so that the water formed in the esterification is separated off continuously via a rectification column mounted on the esterification reactor, the recycling of the cleavage products to the esterification is preferably carried out via this rectification column (recycling is expediently effected into the lower half of the rectification column).

The novel cleavage process can of course also be carried out in a plurality of stages (for example in a cascade, for example as in CN-A 1063678).

Preferably, the novel cleavage is carried out in two stages, the content of acidic cleavage catalysts being brought to, as a rule, from 1 to 20% by weight in the first cleavage stage and from 5 to 40% by weight in the second stage, based on the contained amount of oxyesters to be cleaved. The residence time in the individual stages may be identical or different. Preferably, it increases from the first to the last stage. In a two-stage procedure, the residence time of the cleavage mixture in the first stage is expediently from 1 to 15 h and that in the second stage is from 10 to 40 h.

Furthermore, the cleavage temperature in a multistage procedure preferably increases toward the last stage. In the two-stage case, the cleavage temperature in the first stage is expediently from 160 to 200° C. and that in the second stage is from 180 to 220° C.

The advantage of the stepwise cleavage described above is that the bottom product obtained in the esterification generally still contains significant amounts of the desired ester which, at the high cleavage temperatures, is particularly susceptible to (free radical) polymerization and is not inert even to the acidic cleavage catalysts. Under comparatively mild cleavage conditions in the first stage, these amounts of desired ester may be separated off essentially unchanged with the resulting cleavage products in a mild manner before the cleavage can be completed in the subsequent stages under more severe cleavage conditions. When a multistage cleavage is carried out continuously, the pressure in successive stages may be identical or different. In the case of constant pressure, the transport from one stage to the other may be effected in a simple manner by level-controlled overflow. At different pressures, transport of the mixture by means of pumping is advisable.

In a multistage cleavage, it is furthermore advantageous if the residue of the last cleavage stage is at least partly recycled (expediently from 10 to 80% of its weight) to the first cleavage stage.

Furthermore, different amounts of monomeric and/or oligomeric (meth)acrylic acid, of water and of acidic cleavage catalysts may be fed to the individual stages.

The applicability of the novel cleavage process is not restricted to the special nature of the esterification process, the byproducts of which are the oxyesters, i.e. the addition compounds I and II. As a rule, the esters are prepared by conventional processes (cf. Ullmann's Encyclopedia of Industrial Chemistry, Vol. A1, 5th Ed., VCH, page 167 et seq.). Esterification processes catalyzed by means of ion exchangers are of course also suitable.

A typical example of the conditions under which the esterification preceding the cleavage of the oxyesters can take place may be described briefly as follows:

| | |
|---|---|
| Alcohol: (meth)acrylic acid | 1:0.7–1.2 (molar) |
| Catalyst: | Sulfuric acid or sulfonic acids (e.g. p-toluenesulfonic acid) |
| Amount of catalyst: | 0.1–10% by weight (preferably 0.5–5% by weight), based on starting materials |
| Stabilization: | 200–2000 ppm of phenothiazine (based on the weight of the starting materials) |
| Reaction temperature: | 80–160° C., preferably 90–130° C. |
| Reaction time: | 1–10 h, preferably 1–6 h |

If required, an entraining agent (e.g. cyclohexane or toluene) is used for removing the water of esterification. The esterification may be carried out at atmospheric, superatmospheric or reduced pressure, both continuously and batchwise.

The acrylic acid used for the esterification may have been produced, for example, by catalytic gas-phase oxidation of propene and/or acrolein or propane and may contain typically from 0.05 to 0.5% by weight of aldehydes, from 0.1 to 5% by weight of acetic acid, from 0.05 to 2% by weight of maleic acid/maleic anhydride, from 0.1 to 5% by weight of water, from 0.1 to 1% by weight of polymerization inhibitors (e.g. phenolthiazine), from 0.1 to 5% by weight of oligomeric acrylic acid and from 80 to 99% by weight of acrylic acid.

In the acid-catalyzed esterification of acrylic acid with alkanols, the bottom product resulting after the removal of the acidic esterification catalyst, of the unconverted starting materials and of the acrylic ester has, as a rule, the following composition:

| | |
|---|---|
| 1–20% by weight | of acrylic esters |
| 40–80% by weight | of alkoxypropionates (cf. formula I) |
| 5–30% by weight | of acyloxypropionates (cf. formula II) |
| Remainder: | mainly stabilizers (phenolthiazine) and polymers |
| from 0.1 to 2% by weight | of maleic esters may likewise be present. |

Further details and advantages of the novel process are evident from the embodiments described below.

The advantage of the novel procedure is that the residue remaining after the cleavage and isolation of the cleavage products is generally of pumpable consistency and contains at most a minimum solids load.

EXAMPLES AND COMPARATIVE EXAMPLES

Example 1

A first circulation reactor consisting of glass (volume 1 l), heated by means of a heating cartridge, was filled with 500 g of an oxyester-containing bottom product originating from the preparation of butyl acrylate and freed from the acidic esterification catalyst (below, butyl is generally n-butyl). The bottom product contained 15% by weight of butyl acrylate, 60.5% by weight of butoxyester I (R=C$_4$H$_9$) and 17% by weight of acyloxyester II (R=C$_4$H$_9$). The remainder consisted of (free radical) polymers, oligomers and polymerization inhibitor (phenolthiazine).

60 g of dodecylbenzenesulfonic acid and 95 g of acrylic acid (based on the weight of the acrylic acid stabilized with 300 ppm of phenolthiazine) were then added to the circulation reactor.

180 g of the above bottom product, 40 g of acrylic acid stabilized as above and 20 g of dodecylbenzenesulfonic acid were fed continuously per hour to the circulation reactor filled in this way, the feed being level-controlled.

The cleavage temperature was 175° C. and the pressure was 700 mbar. The cleavage products were removed in vapor form, via a packed column mounted on the circulation reactor (50 cm (packing height)×2.8 cm (internal diameter), 0.8 cm (diameter) Raschig rings) as a splash guard and were condensed. 148 g of condensate were obtained hourly.

The cleavage residue of the first circulation reactor was fed to a second circulation reactor of identical design, the feed being level-controlled (overflow). In addition, 40 g/h of the abovementioned stabilized acrylic acid were fed to the latter reactor. The cleavage temperature in the second circulation reactor was 200° C. The pressure was likewise 700 mbar. The cleavage products of the second circulation reactor were removed as in the case of the first circulation reactor and condensed. 92.5 g of condensate were obtained hourly. The two condensate streams obtained were combined and were analyzed by gas chromatography. According to this, the combined condensate contained (based on its weight):

| | |
|---|---|
| 64.8% by weight | of butyl acrylate, |
| 4.2% by weight | of butanol, |
| 0.2% by weight | of dibutylether and |
| 1.4% by weight | of butenes. |

The conversion in the cleavage was thus 98% by weight, based on the amount of oxyesters contained in the bottom product. The cleavage residue (bottom discharge of the 2nd circulation reactor) was pumpable and contained no solid. Even after the cleavage residue had been stored for 24 hours at 25° C., no solid separated out.

Example 2

A circulation reactor consisting of glass (volume 1 l), heated by means of a heating cartridge, was filled with 500 g of an oxyester-containing bottom product of Example 1, originating from the preparation of butyl acrylate and freed from the acidic esterification catalyst. 60 g of dodecylbenzenesulfonic acid and 95 g of acrylic acid (based on the weight of the acrylic acid stabilized with 300 ppm of phenolthiazine) were then added to the circulation reactor.

95 g of the bottom product of Example 1, originating from the preparation of butyl acrylate, 20 g of acrylic acid stabilized as above and 20 g of dodecylbenzenesulfonic acid were fed continuously per hour to the circulation reactor filled in this way, the feed being level-controlled. The cleavage temperature was 195° C. and the pressure was 700 mbar. The cleavage products were removed as in Example 1, in vapor form, via a packed column mounted on the cleavage reactor (50 cm (packing height) 2.8 cm (internal diameter), 0.8 cm (diameter) Raschig rings) as a splash guard and were condensed. 73 g of condensate were obtained hourly.

According to gas chromatographic analysis, the condensate contained (based on its weight):

| | |
|---|---|
| 61.3% by weight | of butyl acrylate, |
| 4.0% by weight | of butanol, |
| 0.3% by weight | of dibutylether and |
| 2.1% by weight | of butenes. |

The conversion in the cleavage was thus 97% by weight, based on the amount of oxyesters contained in the bottom product. The cleavage residue (bottom discharge) was pumpable and contained no solid. Even after the cleavage residue had been stored for 24 hours at 25° C., no solid separated out.

Comparative Example 1

As in Example 1, except that the dodecylbenzenesulfonic acid was replaced by an equimolar amount of p-toluenesulfonic acid.

The combined condensate contained

| | |
|---|---|
| 64.2% by weight | of butyl acrylate, |
| 4.5% by weight | of butanol, |
| 0.2% by weight | of dibutylether and |
| 1.5% by weight | of butenes. |

The conversion in the cleavage was thus 97% by weight, based on the amount of oxyesters contained in the bottom product. The cleavage residue was pumpable but contained about 1% by weight of solids, some of which separated out when the cleavage residue was left to stand at 25° C.

Comparative Example 2

In a 1 l stirred reactor, a mixture of 180 g of the bottom product of Example 1, originating from the preparation of butyl acrylate, and 120 g of oligomeric acrylic acid stabilized with phenothiazine (bottom product of a distillation of crude acrylic acid) was heated at 700 mbar and 195 0C. The resulting cleavage products were removed via a packed column mounted on the cleavage reactor (30 cm (packing height)×2.8 cm (internal diameter), 0.8 cm (diameter) Rashig rings) as a splash guard and were condensed. 160 g of condensate were obtained in the course of 6.5 hours.

The condensate contained

| 64.0% by weight | of acrylic acid, |
|---|---|
| 26.8% by weight | of butyl acrylate, |
| 0.8% by weight | of butanol and |
| 6.0% by weight | of butyl butoxypropionate. |

The conversion in the cleavage was thus <10% by weight, based on the amount of oxyesters contained in the bottom product.

We claim:

1. A process for esterifying (meth)acrylic acid with an alkanol in the presence of an esterification catalyst, in which unconverted starting compounds and (meth)acrylic ester formed are removed from the reaction mixture by distillation, leaving behind an oxyester-containing bottom product, the bottom product is separated off and the oxyesters contained therein are thereafter cleaved by the action of elevated temperature in the presence of at least one acid catalyst, at least one aromatic sulfonic acid of the formula IV,

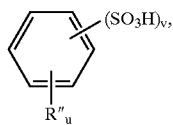

(IV)

where
R" independently of one another are each alkyl of six to twenty carbon atoms,
u is an integer from 1 to 3, and
v is 1 or 2,
being present as the at least one acid catalyst for cleaving the oxyesters, wherein the cleavage is carried out stepwise.

2. A process as claimed in claim 1, wherein the amount of the aromatic sulfonic acids of the formula (IV) is at least 50 mol %, based on the total amount of the acid catalysts used for the cleavage of the oxyesters.

3. A process as claimed in claim 1, wherein the amount of the aromatic sulfonic acids of the formula (IV) is at least 75 mol %, based on the total amount of the acid catalysts used for the cleavage of the oxyesters.

4. A process as claimed in claim 1, wherein the amount of the aromatic sulfonic acids of the formula (IV) is 100 mol %, based on the total amount of the acid catalysts used for the cleavage of the oxyesters.

5. A process as claimed in claim 1, wherein the total amount of acidic cleavage catalysts is from 1 to 50% by weight, based on the amount of the oxyesters to be cleaved.

6. A process as claimed in claim 1, wherein the total amount of acidic cleavage catalysts is from 5 to 20% by weight, based on the amount of the oxyesters to be cleaved.

7. A process as claimed in claim 1, wherein the cleavage of the oxyesters present in the bottom product is effected in the presence of up to 50% by weight, based on the amount of the oxyesters to be cleaved, of monomeric and/or oligomeric (meth)acrylic acid.

8. A process as claimed in claim 1, wherein the cleavage of the oxyesters present in the bottom product is effected in the presence of from 10 to 40% by weight, based on the amount of the oxyesters to be cleaved, of monomeric and/or oligomeric (meth)acrylic acid.

9. A process as claimed in claim 1, wherein the cleavage of the oxyesters present in the bottom product is effected in the presence of from 0.1 to 20% by weight, based on the amount of the oxyesters to be cleaved, of water.

10. A process as claimed in claim 1, wherein the cleavage of the oxyesters present in the bottom product is effected in the presence of from 1 to 10% by weight, based on the amount of the oxyesters to be cleaved, of water.

11. A process as claimed in claim 1, wherein dodecylbenzenesulfonic acid is present as at least one aromatic sulfonic acid of the formula (IV).

12. A process as claimed in claim 1, wherein the cleavage temperature is from 140 to 260° C.

13. A process as claimed in claim 1, wherein the cleavage temperature is from 180 to 230° C.

14. A process as claimed in claim 1, wherein the cleavage is carried out at from 500 mbar to 1 bar.

15. A process as claimed in claim 1, wherein a stripping gas is passed through the bottom product.

16. A process as claimed in claim 1, wherein the stripping gas used is an oxygen-containing gas.

17. A process as claimed in claim 1, wherein the cleavage products obtained are immediately recycled to the esterification.

18. A process as claimed in claim 1, wherein the alkanol is a $C_1$- to $C_8$- alkanol.

19. A process as claimed in claim 1, wherein the alkanol is n-butanol or 2-ethylhexanol.

20. A process as claimed in claim 1, wherein the cleavage is carried out in two stages.

21. A process as claimed in claim 20, wherein the content of acidic cleavage catalysts is from 1 to 20% by weight in the first cleavage stage and from 5 to 40% by weight in the second stage, based on the contained amount of oxyesters to be cleaved.

22. A process as claimed in claim 20, wherein the cleavage temperature in the first stage is from 160 to 200° C. and that in the second stage is from 180 to 220° C.

23. A process as claimed in claim 20, wherein the residence time in the first cleavage stage is from 1 to 15 h and that in the second stage is from 10 to 40 h.

24. A process as claimed in claim 1, wherein the residue of the last cleavage stage is at least partly recycled to the first cleavage stage.

* * * * *